United States Patent [19]

Ayer

[11] Patent Number: 4,693,886
[45] Date of Patent: Sep. 15, 1987

[54] OSMOTIC DEVICE WITH INERT CORE

[75] Inventor: Atul D. Ayer, Mt. View, Calif.

[73] Assignee: Alza Corporation, Palo Alto, Calif.

[21] Appl. No.: 725,840

[22] Filed: Apr. 22, 1985

[51] Int. Cl.[4] .......................... A61K 9/22; A61K 9/24; A61K 9/44
[52] U.S. Cl. ........................................ 424/15; 424/16; 424/21; 604/890; 604/891; 604/892
[58] Field of Search .............................. 424/15, 16, 21; 604/890, 891, 892

[56] References Cited

U.S. PATENT DOCUMENTS

| 2,779,241 | 6/1954 | Howard et al. | 89/1 |
|---|---|---|---|
| 2,801,203 | 7/1957 | Leb et al. | 424/35 |
| 2,853,420 | 9/1958 | Lowery | 424/20 |
| 3,133,132 | 11/1960 | Loeb et al. | 264/49 |
| 3,146,169 | 8/1964 | Stephenson et al. | 424/15 |
| 3,173,876 | 3/1965 | Zobrist | 252/137 |
| 3,184,386 | 5/1965 | Stephenson | 424/21 |
| 3,276,586 | 10/1966 | Rosaen | 210/90 |
| 3,415,225 | 12/1968 | Collier | 424/15 |
| 3,541,005 | 11/1970 | Strathmann et al. | 210/19 |
| 3,541,006 | 11/1970 | Lexington et al. | 210/23 |
| 3,546,142 | 12/1970 | Michaels et al. | 260/2.1 |
| 3,845,770 | 11/1974 | Theeuwes et al. | 128/260 |
| 3,916,899 | 11/1975 | Theeuwes et al. | 128/260 |
| 4,063,064 | 12/1977 | Saunders et al. | 219/121 |
| 4,088,864 | 5/1978 | Theeuwes et al. | 219/121 |
| 4,139,589 | 2/1979 | Beringer et al. | 424/16 |
| 4,160,020 | 7/1979 | Ayer et al. | 424/15 |
| 4,177,256 | 12/1979 | Michaels et al. | 424/22 |
| 4,180,560 | 12/1979 | Katz et al. | 424/16 |
| 4,200,098 | 4/1980 | Ayer et al. | 128/260 |
| 4,218,433 | 8/1980 | Kooichi et al. | 424/15 |
| 4,285,987 | 8/1981 | Aver et al. | 427/3 |
| 4,289,795 | 9/1981 | Bogentoft et al. | 424/21 |
| 4,449,983 | 5/1984 | Cortese et al. | 604/892 |
| 4,454,108 | 6/1984 | Iida et al. | 424/21 |
| 4,503,030 | 3/1985 | Edgren et al. | 424/15 |

Primary Examiner—Shep K. Rose

[57] ABSTRACT

An osmotic dispensing device is disclosed for delivering a medicine to a biological environment of use. The device comprises a semipermeable wall surrounding a compartment with an osmotic passageway in the semipermeable wall connecting the outside of the device with the compartment. The compartment house a medicine releasably held on a carrier member.

11 Claims, 2 Drawing Figures

OSMOTIC DEVICE WITH INERT CORE

FIELD OF THE INVENTION

The present invention pertains to both a novel and useful osmotic device for dispensing a therapeutically effective small amount of a beneficial medicine. More particularly, the invention concerns an osmotic device comprising a compartment containing a small amount of a beneficial medicine carried on an inert core.

BACKGROUND OF THE INVENTION

Osmotic devices for delivering a beneficial medicine to living environments of use are known to the prior art in U.S. Pat. No. 3,845,770, issued to Theeuwes and Higuchi, and in U.S. Pat. No. 3,916,899, issued to the same patentees. The osmotic devices disclosed in these patents comprise a semipermeable wall that surrounds a compartment containing a beneficial medicine. The semipermeable wall is permeable to the passage of an external fluid, and it is substantially impermeable to the passage of medicines. An osmotic passageway is provided through the wall for delivering the beneficial medicine from the device. These prior art devices release the beneficial medicine by imbibing fluid through the semipermeable wall into the compartment, to form in the device an aqueous solution containing the beneficial medicine that is dispensed through the passageway from the device. The external fluid is imbibed through the semipermeable wall into the compartment in a tendency towards osmotic equilibrium, at a rate determined by the permeability of the semipermeable wall and the osmotic pressure gradient across the wall. These devices are extraordinarily effective for delivering a medicament that is soluble in the fluid and exhibit an osmotic pressure gradient across the semipermeable wall against the external fluid, and for delivering a medicament that has limited solubility in the fluid and is admixed with an osmotically effective osmagent that is soluble in the fluid and exhibits an osmotic pressure gradient across the semipermeable wall against the fluid. The beneficial medicament is incorporated into these devices during manufacture, prior to forming the semipermeable wall around the compartment. These prior art osmotic devices generally contained a large amount of medicine, and they operated successfully for delivering the medicine to the environment of use.

Prior to this invention a critical need existed in the pharmaceutical dispensing art for an osmotic device that contained a small amount of medicine and successfully dispensed the medicine to the environment of use. The need existed for an osmotic device that both contained and dispensed small amounts of medicine because many medicines are therapeutically effective in small amounts. The need existed also for an osmotic device that housed smaller amounts of medicine because of the difficulty encountered in formulating a compartment containing a small amount of medicine, and because of the difficulties encountered in surrounding a small amount of medicine with a semipermeable wall.

OBJECTS OF THE INVENTION

It is, accordingly, an immediate object of this invention to provide both a novel and useful osmotic device that fulfills the critical and pressing need of the dispensing art, and which osmotic device also makes a substantial improvement in osmotic systems by providing an osmotic device useful for obtaining better therapy in the management of health and disease.

Another object of the invention is to provide an osmotic dispensing device comprising a compartment containing a therapeutically effective small amount of a beneficial medicine for delivering to a recipient.

Another object of this invention is to provide an osmotic delivery system for delivering a beneficial medicine continuously in a small amount at a controlled rate over a prolonged period of time.

Another object of this invention is to provide an osmotic delivery system comprising a compartment containing a small dosage amount of a beneficial agent.

Another object of this invention is to provide an improvement in an osmotic device comprising a semipermeable wall surrounding a compartment, wherein the improvement comprises a small amount of an orally administrable drug carried on a nontoxic carrier housed in the compartment.

Another object of the invention is to provide an osmotic device comprising a drug coated onto an inert core.

Another object of the invention is to provide an osmotic device comprising a drug compressed onto an inert core.

Another object of the invention is to provide a process for manufacturing an osmotic device comprising a drug carried on an inert core.

Another object of this invention is to provide an osmotic dispensing system comprising a carrier means that is hydrophobic and is formed of a member selected from the group consisting of an inert compressed composition of hydrophobic core forming materials on a hydrophobic polymer.

Another object of the invention is to provide a method of administering a drug to a warm-blooded animal by orally admitting into the animal an osmotic device comprising a drug supported and carried on an inert core that, when the osmotic device is in use, releases drug from the core at a controlled rate over a prolonged period of time.

Other objects, features aspects and advantages of the invention will be more apparent to those versed in the dispensing art from the following detailed specification taken in conjunction with the drawing figures and the accompanying claims.

BRIEF DESCRIPTION OF THE DRAWINGS

In the drawings, which are not drawn to scale, but are set forth to illustrate various embodiments of the invention, the drawing figures are as follows.

In the drawings and in the specification like parts in related figures are identified by like parts. The terms appearing earlier in the specification and in the description of the drawing figures, as well as embodiments thereof, are further detailed elsewhere in the disclosure.

DETAILED DESCRIPTION OF THE DRAWINGS

Figure 1:
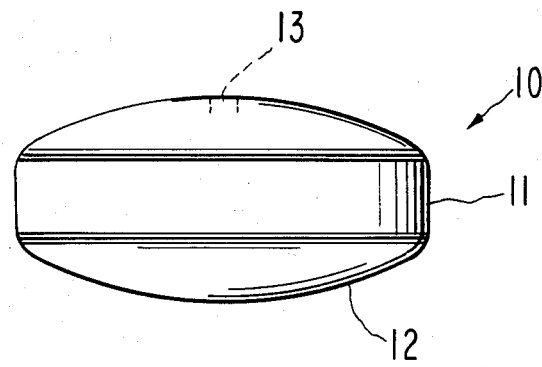
FIG. 1, is a view of an osmotic dispensing device designed for orally administering a beneficial medicine to the gastrointestinal tract; and, FIG. 2, is an opened view of the osmotic dispensing device of FIG. 1, with FIG. 2 illustrating the internal and the external structure of the osmotic dispensing device.
Figure 2:
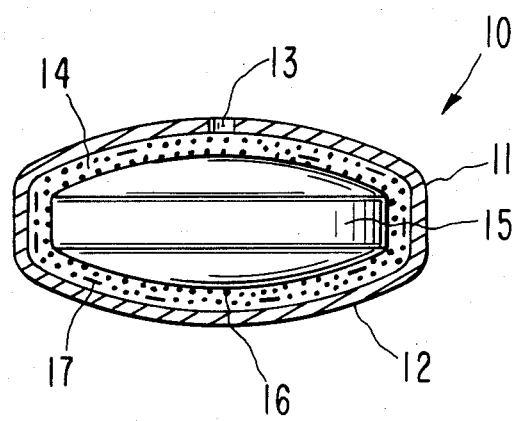

Turning now to the drawings in detail, which are an example of an osmotic dispensing device provided by the invention and which drawing figures are not to be construed as limiting, one example of an osmotic dispensing device is seen in FIGS. 1 and 2. In FIG. 1, osmotic device 10 is seen comprising a body member 11 having a wall 12 that surrounds and forms an internal compartment not seen in FIG. 1. Dispensing device 10 is provided with a passageway 13 in wall 12, which passageway 13 connects the exterior of device 10 with the interior of device 10.

In FIG. 2, dispensing device 10 is seen in opened section. In FIG. 2, device 10 comprises body 11, wall 12, osmotic passageway 13 and an internal compartment 14. Wall 12 is formed of a polymeric composition that is totally or in at least a part permeable to the passage of an external fluid and it is substantially impermeable to the passage of a beneficial medicine. The polymeric composition forming wall 12 is nontoxic and it maintains its physical and chemical integrity during the dispensing life of device 10.

Internal compartment 14 houses an inner core 15. Core 15 can have any geometric shape, and core 15 in a presently preferred embodiment possesses a shape that corresponds to the interior shape of osmotic device 10. Core 15 in a presently preferred embodiment is a carrier means for medicine 16. In this embodiment core 15 provides physical support for a small dosage unit amount of medicine 16. Core 15 in another embodiment is a means for occupying space inside compartment 14. In this latter embodiment core 15 provides space for serving as a carrier for medicine 16. Core 15 serves to limit the space available for diluting medicine 16 with fluid imbibed into compartment 14, thereby prolonging the formation of a saturated solution of medicine 16 and concomitantly prolonging the zero order rate of release of medicine 16 from device 10.

Medicine 16, as represented by dots and supported on carrier means 15, can be from insoluble to very soluble in an aqueous-type fluid, which includes biological fluid. Medicine 16 when soluble exhibits an osmotic pressure gradient across wall 12 against an external fluid that is imbibed into compartment 14. When the beneficial agent has limited solubility in the external fluid it can be mixed with an osmagent 17 and coated onto carrier means 15. In this embodiment osmagent 17 is soluble in the external fluid and it exhibits an osmotic pressure gradient across wall 12 against the external fluid. In operation device 10 containing medicine formulation 16 releases said medicine by fluid being imbibed into compartment 14 in a tendency towards osmotic equilibrium at a rate determined by the permeability of wall 12 and the osmotic pressure gradient across wall 12. The imbibed fluid continuously forms a solution containing the active medicine, or a solution of osmagent containing active medicine in suspension, which solution in either instance is released by the combined operation of device 10. These operations include the solution being osmotically and hydrodynamically delivered through passageway 13 to the biological environment of use.

FIGS. 1 and 2 depict one presently preferred embodiment of device 10. In this embodiment device 10 is made for oral use, that is, for releasing a locally acting medicine, or a systemically acting medicine in the gastrointestinal tract. The oral system can have various shapes and sizes. In one design, device 10 can be curved, such as round, with a diameter of ⅛ inch to 9/16 inch, or it can be shaped like a capsule having a range of sizes from triple zero to zero, and from 1 to 8.

While FIGS. 1 and 2 illustrate one dispensing device that can be made according to the invention, it is to be understood device 10 can take a wide variety of shapes, sizes and forms for delivering a beneficial medicine to the environment of use. For example, the devices includes buccal, implant, artificial gland, cervical, intrauterine, nose, and the like. In these forms device 10 can be adapted for administering a beneficial medicine to numerous animals, warm-blooded mammals, humans, avians and reptiles. The device also can be sized, shaped, structured and adapted for delivering an active agent in streams, aquariums, fields, factories, reservoirs, laboratory facilites, hot houses, transportation means, naval means, military means, hospitals, veterinary clinics, nursing homes, farms, zoos, sickrooms, chemical reactions and over environments of use.

DETAILED DESCRIPTION OF THE INVENTION

In accordance with the practice of the invention, it now has been found that osmotic delivery device 10 can be manufactured with a wall 12 formed of a material that does not adversely affect medicine 16 which includes drug, an osmagent, an animal, or a host, and wall 12 is permeable to the passage of an external aqueous type fluid such as water and biological fluids, while remaining essentially impermeable to the passage of medicine 16 which includes drug, osmagent, and the like. The selectively semipermeable materials forming wall 12 are insoluble in fluids, and they are non-erodible, hence, they maintain their physical and chemical integrity during operation in the environment of use.

Typical materials for forming wall 12 include semipermeable polymers known to the art as osmosis and reverse osmosis membranes. These include cellulose ester, cellulose ether, cellulose ester-ether, cellulose acylate, cellulose diacylate, cellulose triacylate, cellulose acetate, cellulose diacetate, cellulose triacetate, agar acetate, amylose triacetate, beta glucan acetate, cellulose acetaldehyde dimethyl acetate, cellulose acetate ethyl carbamate, cellulose acetate methyl carbamate, cellulose acetate succinate, cellulose acetate dimethylaminoacetate, cellulose acetate ethyl carbamate, cellulose acetate chloroacetate, cellulose dipalmate, cellulose dioctanoate, cellulose dicaprylate, cellulose dipentanlate, cellulose acetate valerate, cellulose acetate succinate, cellulose propionate succinate, cellulose acetate p-toluene sulfonate, cellulose acetate butyrate, cross linked selectively semipermeable polymers formed by the coprecipitation of a polyanion and a polycation as disclosed in U.S. Pat. Nos. 3,173,876; 3,276,586; 3,541,005; 3,541,006, and 3,546,142; semipermeable polymers as disclosed by Loeb and Sourirajan in U.S. Pat. No. 3,133,132; lightly cross linked polystyrene derivative, cross linked poly(sodium styrene sulfonate), poly(vinylbenzyltrimethylammonium chloride), cellulose acetate having a degree of substitution up to 1 and an acetyl content up to 21%, cellulose diacetate having a degree of substitution of 1 to 2 and an acetyl content of 21 to 35%, cellulose triacetate having a degree of substitution of 2 to 3 and an acetyl content of 35 to 44.8%, as disclosed in U.S. Pat. No. 4,160,020. Generally, semipermeable materials useful for forming wall 12 will have a fluid permeability of $10^{-5}$ to $10^{-1}$ (cc mil/cm$^1$ hr/atm) expressed per atmosphere of hydrostatic or osmotic pressure difference across semipermeable wall 12 can be used for the intended purpose.

The expression "core 15" and, as used for the purpose of this invention, its equivalent core means and carrier means generically denote a material or a compositon of matter which, in both embodiments, is non-toxic and is inert. The term "inert" means the core 15 is free of physiological and pharmacological properties; that is, core member 15 does not possess any therapeutic activity. Core member 15 in a presently preferred embodiment is hydrophobic; that is, core member 15 lacks affinity for water, and it does not substantially absorb or imbibe aqueous type fluids. Core member 15 is, for example, a member selected from starches including hydroxypropyl starch, corn starch and potato starch; a member selected from the group consisting of cellulose, calcium hydrogen phosphate, calcium carbonate, aluminum silicate, magnesium metasilicate aluminate; and a member selected from olefins and vinyl polymers such as polyethylene, polypropylene, polystyrene; condensation polymers such as polyamides, polyesters, polyurea-formaldehyde and the like. Core member 15 can comprise a multiplicity of granules of a material that is compressed into a unit mass, then coated with a medicinal formulation, or core 15 can be a single member such as a preshaped, precut section of a polymer then coated with the medicine formulation.

The expression "beneficial medicine 16" and "beneficial medicine formulation" as used herein denotes a beneficial drug neat, and a composition comprising a beneficial drug and an osmagent. In the specification and the accompanying claims, the term "medicine" includes drug, and the term "drug" includes any physiologically or pharmacologically active substance that produces a local or systemic effect, in animals, including warm-blooded mammals; humans and primates; fishes; reptiles and zoo animals. The term "physiologically" as used herein denotes the administration of a drug to produce normal levels and functions. The term "pharmacologically" denotes variations in response to amount of drug administered to the host. *Stedman's Medical Dictionary*, 1966, published by Williams and Wilkins, Baltimore, MD. The active drug that can be delivered includes inorganic and organic drugs without limitations, those drugs that act on the central nervous system, depressants, hypnotics, sedatives, psychic energizers, tranquilizers, anticonvulsants, muscle relaxants, anti-parkinson agents, analgesics, anti-inflammatory, local anesthetics, muscle contractants, anti-microbials, anti-malarials, hormonal agents, contraceptives, sympathomimetics, diuretics, anti-parasitics, neo-plastics, hypoglycemics, ophthalmics, electrolytes, diagnostic agents, and cardiovascular drugs. The amount of medicine carried, coated or compressed onto core means 15 generally is from 0.1 mg to 125 mg of medicine.

Exemplary drugs that can be carried on the core member and delivered by the osmotic device of this invention include prochlorperazine edisylate, prochlorperazine maleate, prazosin hydrochloride, clonidine hydrochloride, hydralazine hydrochloride, dextromethorpan hydrobromine, dextroamphetamine phosphate, diethylpropionm hydrochloride, isoxsuprine hydrochloride, ambenonium chloride, phenoxybenzamine hydrochloride, phentolamine hydrochloride, guanethidine sulfate, clidinium bromide, glycopyrrolate, homatropine methylbromide, hyoscyamine hydrobromide, mepenzolate bromide, methscopolamine bromide, balofen, and the like. These drugs and their daily dose are known to the art in *Pharmaceutical Sciences* by Remington, 16th Ed., 1980, published by Mack Publishing Company, Easton, PA.

The medicine can be in various forms, such as uncharged molecules, molecular complexes, pharmacologically acceptable salts such as hydrochlorides, hydrobromides, sulfate, laurylate, palmitate, phosphate, nitrite, borate, acetate, maleate, tartrate, oleate and salicylate. For acid medicine, salts of methals, amines or organic cations, for example, quaternary ammonium can be used. Derivatives of medicine such as esters, ethers and amides can be used. Also, a medicine that is water insoluble can be used in a form that is a water soluble derivative thereof to serve as a solute and, on its release from the device, is converted by enzymes, hydrolyzed by body pH or other metabolic process to the original biologically active form.

The osmagent present in the device, when used according to the mode of the invention, are osmotically effective compounds soluble in fluid that enter the device and exhibit an osmotic pressure gradient across the semipermeable wall against the exterior fluid. Osmotically effective osmagents useful for the present purpose include magnesium sulfate, magnesium chloride, sodium chloride, lithium chloride, potassium sulfate, sodium carbonate, sodium sulfite, lithium sulfate, potassium chloride, sodium sulfate, d-mannitol, urea, inositol, raffinose, glycose, mixtures thereof, and the like. The osmagent is usually present in an excess amount, and it can be in any physical forms, such as particle, powder, granule, and the like. The osmotic pressure in atmospheres, ATM, of the osmagents suitable for the invention will be greater than zero ATM, generally from zero ATM up to 500 ATM, or higher. The osmotically effective compounds are known to the art in U.S. Pat. Nos. 4,177,256 and 4,449,983.

The solubility of a medicine in the fluid that enters the compartment can be determined by known techniques. One method consists of preparing a saturated solution comprising the fluid plus the medicine as ascertained by analyzing the amount of medicine present in a definite quantity of the fluid. A simple apparatus for this purpose consists of a test tube of medium size fastened upright in a water bath maintained at constant temperature and pressure, in which the fluid and medicine are placed and stirred by a rotating glass spiral. After a given period of stirring, a weight of the fluid is analyzed and the stirring continued an additional period of time. If the analysis shows no increase of dissolved medicine after successive periods of stirring, in the presence of excess solid medicine in the fluid, the solution is saturated and the results are taken as the solubility of the produce in the fluid. If the medicine is soluble, an added osmotically effective compound optionally may not be needed. If the medicine has limited solubility in the fluid, then an osmotically effective compound can be incorporated into the device. Numerous other methods are available for the determination of the solubility of an agent in a fluid. Typical methods used for the measurement of solubility are chemical and electrical conductivity. Details of various methods for determining solubilities are described in *United States Public Health Service Bulletin*, No. 67 of the Hygenic Laboratory; *Encyclopedia of Science and Technology*, Vol. 12, pages 542 to 556, 1971, published by McGraw-Hill, Inc.; and *Encyclopedia Dictionary of Physics*, Vol. 6, pages 547 to 557, 1962, published by Pergammon Press, Inc.

The expression "osmotic passageway" as used herein comprises means and methods suitable for releasing a beneficial agent including a medicine from compartment 14. The osmotic passageway or orifice will pass through the wall for communicating with compartment 14. The expression "passageway" includes aperture, orifice, bore, pore, porous element through which a beneficial agent can migrate, hollow fiber, capillary tube, and the like. The expression also includes a material that erodes in the environment of use to produce a passageway in the device. Representative materials suitable for forming a passageway include an erodible poly(glycolic) and poly(lactic) acids in the wall, gelatinous filaments, poly(vinyl alcohol), and the like. The passageway can be formed by leaching a material such as sorbitol from the wall. The passageway can have any shape. For example, round, triangular, square, elliptical, irregular, and the like. Also, the device can be constructed with one or more passageways. In an embodiment when the device is fabricated with more than one passageway they can be construed as the functional equivalent in an operative embodiment of a single osmotic passageway. The expression "osmotic passageway" includes passageways formed by mechanical drilling or laser drilling through the wall. Generally, for the purpose of this invention, the passageway will have a maximum cross-sectional area, A, defined by equation 1:

$$\frac{L}{F} \times \frac{Qv}{t} \times \frac{1}{DS} \tag{1}$$

wherein L is the length of the passageway, (Qv/t) is the mass delivery rate of the agent D released per unit of time, D is the diffusion coefficient of the medicine in the release solution, S is the solubility of the medicine in the fluid and F has a value of approximately 2 to 1000, said osmotic passageway having a minimum area, $A_s$, defined by equation 2:

$$\left[ \frac{Lv}{t} \times 8 \times \frac{\pi \eta}{\Delta P} \right] /12 \tag{2}$$

wherein L is the length of the passageway, v/t is the volume of the medicine released per unit of time, $\pi$ is 3.14, $\eta$ is the viscosity of the solution being released, and $\Delta P$ is the hydrostatic pressure difference between the inside and the outside of the compartment and having a value up to 20 atm. The dimension for the osmotic passageway is disclosed in U.S. Pat. No. 3,916,899. Laser drilling equipment having photo detection means for orienting a device for surface selected drilling are known in U.S. Pat. No. 4,063,064 and U.S. Pat. No. 4,088,864.

The osmotic device of the invention is maufactured using standard machines. For example, in one embodiment a plurality of core forming particles are compressed under a pressure head up to 50 tons into a solid, compacted mass and then coated with a medicine. In another embodiment, a polymer is cut into a shape corresponding to the shape of a compartment of an osmotic device and then the shaped and sized core member is coated with a medicine formulation. In another embodiment a medicine and an osmagent and, optionally, other ingredients that may be housed in the compartment of an osmotic device, are blended to form a homogeneous composition and then pressed onto a solid core possessing dimensions that correspond to the internal dimensions of the area to be occupied in the compartment. The various ingredients can be mixed with a solvent by ballmilling, calendering, stirring or rollmilling, and then pressed onto the preselected shaped core. In another manufacture the medicine can be coated by dipping or air suspension coating onto the core member. The semipermeable wall can be applied around the medicine core by molding, spraying or dipping the medicine coated, pressed shapes into a wall forming material. Another presently preferred technique that can be used for applying the wall is the air suspension procedure. This procedure consists in suspending and tumbling the medicine coated core in a current of air and a wall forming composition until the wall is applied to the composite. The air suspension procedure is described in U.S. Pat. No. 2,779,241; *J. Am. Pharm. Assoc.*, Vol. 48, pages 451 to 459, 1979, and ibid, Vol. 49, pages 82 to 84, 1960. Other standard manufacturing procedures are described in *Modern Plastics Encyclopedia*, Vol. 46, pages 62 to 70, 1969; and in *Pharmaceutical Sciences*, by Remington, 14th Ed., pages 1626 to 1678, published by Mack Publishing Company, Easton, PA.

Exemplary solvent suitable for manufacturing the wall and the core include inorganic and organic solvents that do not adversely harm the core and the wall forming material, and the final device. The solvents broadly include members selected from the group consisting of aqueous solvents, alchols, ketones, esters, ethers, aliphatic hydrocarbons, halogenated solvents, cycloaliphatic, aromatics, heterocyclic solvents, and mixtures thereof. Typical solvents include acetone, diacetone alcohol, methanol, ethanol, isopropyl alcohol, butyl alcohol, methyl acetate, ethyl acetate, isopropyl acetate, n-butyl acetate, methyl isobutyl ketone, methyl propyl ketone, n-hexane, n-heptane, ethylene glycol monoethyl ether, ethelene glycol monoethyl acetate, methylene dichloride, ethylene dichloride, propylene dichloride, carbon tetrachloride, nitroethane, nitropropane, tetrachloroethane, ethyl ether, isopropyl ether, cyclohexane, cyclo-octane, benzene toluene, naphtha, 1,4-dioxane, tetrahydrofuran, diglyme, water, and mixtures there of such as acetone and water, acetone and methanol, acetone and ethyl alcohol, methylene dichloride and methanol, and ethylene dichloride and methanol, and the like.

The following example illustrates means and methods for carrying out the present invention. The example is merely illustrative and it should not be considered as limiting the scope of the invention, as this example and other equivalents thereof will become more apparent to those versed in the dispensing art in the light of the present disclosure, the drawings and the accompanying claims.

EXAMPLE 1

An osmotic dispensing device for delivering the beneficial medicine potassium chloride at an osmotically controlled rate is manufactured as follows.

I. Inert core fabrication. First, 980 grams of barium sulfate is added slowly to 150 grams of ethyl cellulose in 500 milliliters of isopropyl alcohol and the core-forming ingredients blended in a Hobart mixer for about 30 minutes to form inert granules. The granules are dried at 50° C. for 24 hours, and then passed through a No. 20 mesh sieve. next, the granules are mixed with 0.5% magnesium stearate and blended for 5 minutes. The granules are then pressed into a core adapted, shaped and sized into a core using a standard tabletting machine with a 7/16 inch diameter punch. The cores formed by this procedure weighed 625 mg.

II. Medicine formulation. Next, a medicine formulation for coating onto the inert cores is prepared by thoroughly dissolving 190 grams of potassium chloride and 47 grams of hydroxypropyl methylcellulose in 2133 millileters of distilled water.

III. Coating of inert cores. The barium sulfate inert cores were placed in an air suspension machine and each core was coated with 0.05 mg of the potassium chloride formulation.

IV. Rate controlling semipermeable wall. First, 100 grams of cellulose acetate having an acetyl content of 39.8% is dissolved in 1900 grams of methylene chloride:methanol solvent, (90:10 by weight). The inert cores coated with the potassium chloride were surrounded with a cellulose acetate wall in an air suspension machine until each core-drug formulation was surrounded with a semipermeable wall that weighted 35 mg. The osmotic dispensing devices next are dried in a forced air oven for 48 hours at 50° C., to free the devices of solvent. Then, an osmotic passageway is drilled through the semipermeable wall connecting the exterior of the device with the medicine formulation. The passageway has a diameter of 0.26 mm and the device has a rate of release of about 14 milligrams per hour.

EXAMPLE 2

An osmotic delivery device for the controlled delivery of the beneficial drug salbutamol sulfate, a bronchodilator, is prepared as follows.

I. A formulation comprising 70% salbutamol sulfate, 25% hydroxypropyl methylcellulose and 5% polyvinyl pyrrolidone is dissolved in an organic solvent consisting essentially of methylene chloride:methanol, (60:40 by weight), to yield a coating solution containing 8% solids.

II. Then, a plurality of cores each weighing 275 mg, having a diameter of ⅜ inch and made of Teflon ®, a tetrafluoroethylene homopolymer, are coated with the drug formulation in an air suspension machine.

III. Next, the drug coated cores are surrounded with a semipermeable wall. The wall is formed from a wall-forming composition comprising cellulose acetate having an acetyl content of 39.8% dissolved in a solvent comprising methylene chloride:methanol (90:10 by weight), to obtain a coating solution comprising 5% solid. Each core is surrounded with the semipermeable wall forming composition until the wall weighs about 18 mg.

IV. The osmotic devices are removed from the air suspension coater and dried in a forced air oven for 48 hours at 50° C. Then, after cooling to room temperature a 0.26 mm osmotic passageway is laser drilled through the semipermeable wall. The osmotic system, when placed in artificial gastric fluid for 4 hours and in artificial intestinal fluid for 10 hours, exhibited an average rate of release of 0.85 mg/hr of salbutamol sulfate.

EXAMPLE 3

A non-stirring rate osmotic device that releases drug independent of the pH of the environment is manufactured by following the procedures described immediately above. In the present example, the cores consisted of 95% calcium carbonate, 4% ethyl cellulose and 1% magnesium stearate. The compressed oval cores are coated with a medicinal formulation comprising 5.6% haloperidol, 25% hydroxypropyl methylcellulose, 5% polyvinyl pyrrolidone and 64.4% succinic acid dissolved in methylene chloride:methanol, (50:50 by volume), to obtain 3% solid. The cores are air coated with 1 mg of haloperidol per core. The drug-core composites are surrounded with a semipermeable wall with the following wall-forming composition: 90% cellulose acetate having an acetyl content of 39.8%, 5% polyethylene glycol having an average molecular weight of 3350, and 5% hydroxypropyl methylcellulose dissolved in methylene chloride:methanol, (88:12 by weight), with a 4% solid composition. Each core is coated with a 26 mg semipermeable formulation wall. After drying, a 0.36 mm osmotic passageway is laser drilled in the semipermeable wall. The osmotic device, when placed in artificial gastric fluid for 4 hours and in artificial intestinal fluid for 10 hours, dispensed 0.09 mg/hr of haloperidol.

EXAMPLE 4

The procedures described in Examples 1 to 3 are followed in this example. In this example, a series of cores weighing 650 mg, having a diameter of 7/16 inches and consisting of compressed calcium carbonate-ethyl cellulose-magnesium stearate, 95%-4%-1% by weight, are coated with a 1 mil thick coat of cellulose acetate having an acetyl content of 39.8%, in an accelacoater with an airless spray gun. The core carrier member next are coated with a medicinal formulation comprising 71.205% phenylpropanolamine hydrochloride, 3.795% chloropheniramine maleate, 20% hydroxypropyl methylcellulose and 5% polyvinyl pyrrolidone in methylene chloride:methanol, (60:40 by weight, 5% solids). Each core carrier member is coated until 75 mg of phenylpropanolamine hydrochloride and 4 mg of chloropheniramine maleate adhere to the core carrier member. Next, the drug core composites are surrounded with a semipermeable wall using the following wall forming composition, 98% cellulose acetate having an acetyl content of 39.8% and 2% hydroxypropyl methylcellulose dissolved in methylene chloride:methanol (90:10 by weight, 4% solids). Each osmotic system is coated with a 5.3 mil wall. The osmotic systems are dried and a 0.36 mil osmotic passageway is drilled through the semipermeable wall. The osmotic systems release 7.5 mg of phenylpropanol amine hydrochloride and 4 mg of chloropheniramine maleate over a 10 hour delivery period.

EXAMPLES 5 TO 7

The procedures described above are repeated in those examples with conditions as previously described, except that in the present example the drug is chloropheniramine maleate 4 mg, atropine hydrochloride 2 mg, or sodium fluoride 20 mg.

The novel osmotic systems of this invention use means for the obtainment of precise release rates in the environment of use while simultaneously maintaining the integrity and character of the system. While there has been described and pointed out features of the invention as applied to presently preferred embodiments, those skilled in the art will appreciate that various modifications, changes, additions and omissions in the system illustrated and described can be made without departing from the spirit of the invention.

I claim:

1. An osmotic dispensing device for delivering a beneficial medicine formulation to an environment of use, comprising:

(a) a wall comprising in at least a part a semipermeable composition permeable to the passage of an exterior fluid present in the environment of use and substantially impermeable to the passage of the beneficial medicine formulation, the wall surrounding and forming;

(b) a compartment;

(c) means in the compartment for carrying a beneficial medicine formulation, said means comprising a member selected from the group consisting of a nontoxic, physiologically and pharmacologically inert hydrophobic composition and a nontoxic, physiologically and pharmacologically inert hydrophobic polymer, which means comprises a preshape that corresponds to the interior shape of the osmotic dispensing device thereby providing support for a medicinal formulation;

(d) a dosage unit amount of a medicine formulation carried on the means; and, (e) at least one passageway in the wall communicating with the compartment for delivering the beneficial medicine formulation from the osmotic device.

2. The osmotic dispensing device for delivering a beneficial medicine formulation to an environment of use according to claim 1, wherein the means is essentially insoluble in aqueous fluids.

3. The osmotic dispensing device for delivering a beneficial medicine formulation to an environment of use according to claim 1, wherein the medicine formulation carried on the means is releasably coated on the means.

4. The osmotic dispensing device for delivering a beneficial medicine formulation to an environment of use according to claim 1, wherein the means is a compressed core.

5. The osmotic dispensing device for delivering a beneficial medicine formulation to an environment of use according to claim 1, wherein the means is a water insoluble polymer.

6. The osmotic dispensing device for delivering a beneficial medicine formulation to an environment of use according to claim 1, wherein the means possesses a shape corresponding to the internal shape of the compartment.

7. The osmotic dispensing device for delivering a beneficial medicine formulation to an environment of use according to claim 1, wherein the means is shaped, sized and adapted for placement in the osmotic dispensing device.

8. A process for manufacturing an osmotic dispensing device for delivering a medicine to a fluid environment of use, the process comprising:

(a) compressing at least one water insoluble, nontoxic inert material into a solid, hard core;

(b) coating the compressed core with a first coat comprising a medicine formulation to form a medicine coated core;

(c) surrounding the medicine coated core with a semipermeable wall; and, (d) drilling a passageway in the wall connecting the exterior of the device with the interior of the device for releasing the medicine through the passageway from the device.

9. A method for delivering a medicinal formulation to a fluid environment of use, wherein the method comprises:

(a) admitting into the fluid environment of use an osmotic dispensing device comprising:

(1) a wall formed of a semipermeable composition permeable to the passage of fluid present in the environment of use and substantially impermeable to a medicinal formulation surrounding and defining:

(2) a compartment;

(3) carrier means in the compartment for supporting a medicinal formulation;

(4) a medicinal formulation carried on the carrier means; and, (5) an osmotic calibrated passageway in the wall communicating the fluid environment with the compartment for releasing the medicine formulation from the device;

(b) imbibing fluid from the environment into the compartment to form a solution containing the medicine formulation; and, (c) delivering the medicine formulation through the passageway to the fluid environment of use.

10. The method for delivering the medicinal formulation to a fluid environment of use according to claim 9, wherein the passageway comprises at least one pore.

11. The method for delivering the medicinal formulation to a fluid environment of use according to claim 9, wherein the passageway comprises a porous element.

* * * * *